US00PP11086P

United States Patent [19]

Bull

[11] Patent Number: Plant 11,086

[45] Date of Patent: Oct. 12, 1999

[54] NEW GUINEA IMPATIENS PLANT NAMED 'JENNIFER'

[76] Inventor: Norbert Bull, Gaertnersiedlung 2, 24610 Goennebek, Germany

[21] Appl. No.: 08/881,084

[22] Filed: Jun. 23, 1997

[30] Foreign Application Priority Data

Nov. 20, 1996 [DE] Germany ..... IM 414

[51] Int. Cl.[6] ..... A01H 5/00

[52] U.S. Cl. ..... Plt./318

[58] Field of Search ..... Plt./87.6, 318

[56] References Cited

U.S. PATENT DOCUMENTS

P.P. 8,360 8/1993 Bull ..... Plt./87.6

*Primary Examiner*—Lynette F. Smith
*Assistant Examiner*—Kent L. Bell
*Attorney, Agent, or Firm*—Foley & Lardner

[57] ABSTRACT

A new and distinct cultivar of New Guinea Impatiens plant named 'Jennifer', characterized by its light violet flower color, numerous medium sized flowers, light to medium green foliage, narrow elliptical shaped leaves,small plant habit with weak growth habit, and medium flowering response.

1 Drawing Sheet

The present invention comprises a new and distinict cultivar of New Guinea Impatiens, referred to by the cultivar name 'Jennifer'.

'Jennifer' is a product of a planned breeding program and was orginated from a hybridization made by the inventor Norbert Bull in a contrtolled breeding program in Goennebek, Germany, in 1993. The female parent was a seedling designated no. 1 and the male parent was a seedling designated no. 5. Both parents are proprietary cultivars used in the breeding program.

'Jennifer' was discovered and selected as one flowering plant within the progeny of the stated cross by the inventor in 1994 in a controlled environment in Goennebek, Germany.

The first act of vegetative or asexual reproduction of 'Jennifer' was accomplished when cuttings were taken from the initial selection in Autumn 1994 in a controlled environment in Goennebek by, or under the supervision of, Norbert Bull.

Horticultural examination of plants grown from these cuttings initiated in Spring 1995 in Goennebek, Germany, and continuing thereafter. has demonstrated that the combination of characteristics as herein disclosed for 'Jennifer' are firmly fixed and are retained through successive generations of a sexual reproduction.

'Jennifer' has not been observed under all possible environmental conditions. The phenotype may vary significantly with variations in environment such as temperature, light intensity and day length, without, however, any variation in genotype.

the following observations, measurements, and comparisons describe plants grown in Hillscheid, Federal Republic of Germany under greenhouse conditions which approximate those generally used in commercial practice.

The following traits have been repeatedly observed and are determined to be basic characteristics of 'Jennifer', which in combination distinguish this impatiens as a new and distinct cultivar:

1. Light violet flower color
2. Numerous medium sized flowers
3. Light to medium green foliage
4. Narrow elliptical shaped leaves
5. Small plant habit, weak growth
6. Medium flowering response
7. Resistant to powdery mildew Of the many commerical cultivars known to the present inventor, the most similar in comparison to 'Jennifer' are the commercial cultivar 'Sonjana' (unpatented) and the cultivar 'Light Lavender II' (U.S. Plant Pat. No. 9,278). In comparison to 'Sonjana', 'Jennifer' has a more intense flower color, its flowers are more above the foliage (less covered by leaves), and appears to be generally more disease resistant during the cultivation period.

In comparison to 'Light Lavender II', 'Jennifer' has a more intense violet flower color, and lacks the distinct white eye of 'Light Lavender II'. Leaves of 'Jennifer' are narrower, and plant habit is considerably lower, the height of 'Jennifer' being 11 cm as opposed to 15 cm for 'Light Lavender II'.

The accompanying colored photographic drawing shows typical flower and foliage characteristics of 'Jennifer', with colors being as true as possible with illustrations of this type. In this regard, the colors in the illustration appear lighter than the actual R.H.S. values for 'Jennifer'. The lighting is bright as to give the appearance of lighter, less-intense hues.

In the following description color references are made to The Royal Horticultural Society Colour Chart. The color values were determined indoors from flowers taken from plants grown in Hillscheid, Federal Republic of Germany, under greenhouse conditions which approximate those generally used in commercial practice.

The description is based on plants which were planted as rooted cuttings in 10 cm pots in early March and then grown in greenhouse at 20° C minimum temperature.

Classification:

*Botanical.*—A hybrid of the genus Impatiens.

*Commercial.*—New Guinea Impatiens cv 'Jennifer'.

Plant

General appearance and form:

*Habit.*—Compact, uniformly molded, self-branching, and growth is indeterminate, although weak after flowering begins.

*Height.*—11 cm.

*Width.*—25 cm.

*Internode lenght.*—15–20 mm.

*Stem color.*—Mainly green, pink at the base of nodes.

*Flowering response.*—8–9weeks after planting of rooted cuttings.

*Flowering season.*—Generally indeterminate, mainly from March to October, depending on light intensity.

*Lasting quality of the bloom.*—Up to a least three weeks,

*Propagation.*—Usually terminal tips for cuttings.

*Rooting.*—Color is R.H.S. 159 B-C; roots initiate in about 18 days at 22 C, from sticking to transplanting; no distinguishing rooting habit.

Foliage:

*Leaf arrangement.*—Primarily in whorls, leaves are distinctly upwardly directed.

*Shape of leaf.*—Narrow, elliptic with acute base and slightly acuminate apex.

*Margin.*—Slightly serrated, ciliated.

*Leaf, length.*—About 135 mm.

*Leaf, width.*—37–40 mm.

*Main color of upper surface.*—Light to medium green, approximately R.H.S. 137 C-D.

*Veins on upper surface, color.*—very light brownish pink near the base of the leaf, about 48 B, light green from the base to the tip.

*Variegation on leaf.*—Absent.

*Main color of lower surface.*—Light green, about R.H.S. 138 B-C.

*Veins on lower surface, color.*—Mainly greenish-white, about 157 D.

*Petiole, length.*—About 30 mm.

*Petiole, color.*—Light green, pink lined.

INFLORESCENCE

Flower:

*Flower number per node.*—About 5–7, in various stages of development, usually one flower per leaf.

*Form of corolla.*—Single 5 petals per flower.

*Shape.*—Zygomorph, often somewhat cupped.

*Average length.*—58 mm.

*Average width.*—55 mm.

*Color* (*general tonality from a distance of three meters*) .—Violet to light violet.

*Petal number.*—Five (5).

*Petal shape.*—Roughly heart-shaped, moderately lobed, upper petal curved.

*Petal size.* Upper, lower, and side petals are about 18–30 mm in width; the petal length is about 30 mm.

*Petal texture.*—Smooth, slightly glossy.

*Main color of upper surface.*—R.H.S. 78 A, may later fade to R.H.S. 78 B.

*Color of lower surface.*—R.H.S. 78 B.

*Eye zone.*—Very weak, purple R.H.S. 74 B.

*Spur shape and size.*—Downwardly curved, about 45–50 mm in length.

*Spur, color.*—R.H.S. 63 A or lighter.

*Pedicel, length.*—About 30–35 mm.

*Pedicel, color.*—Light green, 144 C.

Reproductive organs:

*Androecium.*—Stamens: Five (5) in number, fused upper surface color is about R.H.S. 74 C. Anthers: Hooded, color is about R.H.S. 11 D. Pollen: Color is about R.H.S. 4 D.

*Gynoecium.*—Stigma and style: Five (5) in number, very short, nearly colorless, about R.H.S. 11 D.

*Ovary.*—Five (5) celled, 3–5 mm in length, surface color is about RHS 137 C–D.

I claim:

1. A new and distinct cultivar of New Guinea Impatiens plant named 'Jennifer', as illustrated and described.

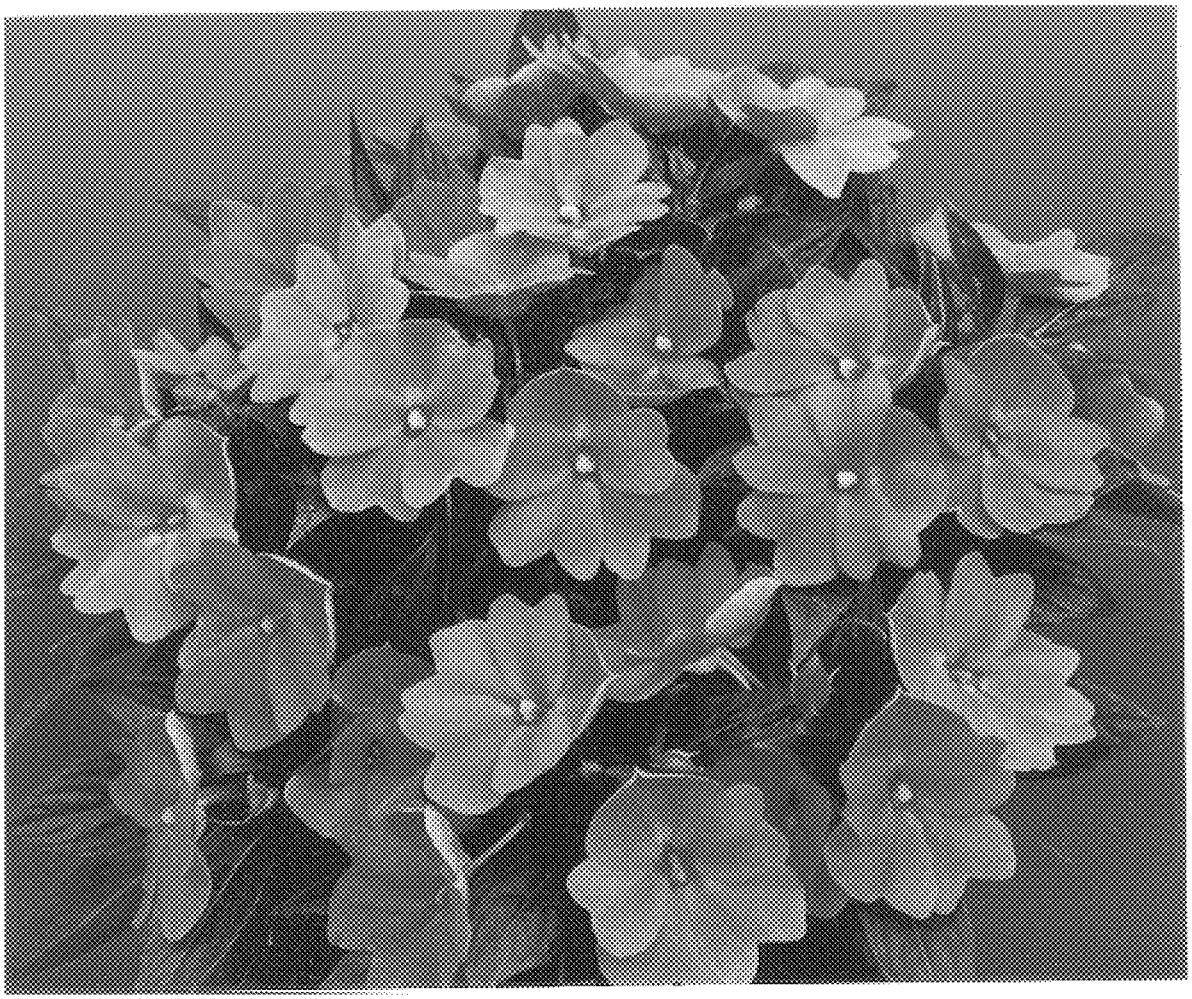

* * * * *